US012569699B1

(12) United States Patent
    Wang

(10) Patent No.: US 12,569,699 B1
(45) Date of Patent: Mar. 10, 2026

(54) ADJUSTABLE LIGHT THERAPY CARE ELECTRIC TOOTHBRUSH

(71) Applicant: Shenzhen Besman Electronic Technology Co., LTD, Shenzhen (CN)

(72) Inventor: Xuewu Wang, Shenzhen (CN)

(73) Assignee: Shenzhen Besman Electronic Technology Co., LTD, Shenzhen (CN)

( * ) Notice: Subject to any disclaimer, the term of this patent is extended or adjusted under 35 U.S.C. 154(b) by 0 days.

(21) Appl. No.: 19/289,427

(22) Filed: Aug. 4, 2025

(30) Foreign Application Priority Data

Jul. 2, 2025 (CN) .......................... 202521376521.7

(51) Int. Cl.
    *A61C 17/34*      (2006.01)
    *A46B 5/00*       (2006.01)
    *A46B 13/02*      (2006.01)
    *A46B 15/00*      (2006.01)
    *A61N 5/06*       (2006.01)

(52) U.S. Cl.
    CPC .......... *A61N 5/0603* (2013.01); *A46B 5/0095* (2013.01); *A46B 13/02* (2013.01); *A46B 15/0036* (2013.01); *A61C 17/34* (2013.01); *A61C 2204/002* (2013.01); *A61N 2005/0606* (2013.01); *A61N 2005/0663* (2013.01); *A61N 2005/0666* (2013.01)

(58) Field of Classification Search
    CPC ..... A46B 5/0095; A46B 9/04; A46B 15/0036; A61C 17/34; A61N 5/0624
    See application file for complete search history.

(56)                  References Cited

U.S. PATENT DOCUMENTS

2022/0211166 A1*  7/2022  Wagner ................ A61C 17/222
2024/0374022 A1*  11/2024  Dishon ............. A46B 15/0028
2025/0024935 A1*  1/2025  Liu ...................... A61C 17/221

FOREIGN PATENT DOCUMENTS

CN       211094892 U    7/2020
CN       117598825 A    2/2024
CN       119157653 A    12/2024

* cited by examiner

*Primary Examiner* — Michael D Jennings
(74) *Attorney, Agent, or Firm* — Nitin Kaushik

(57)                  ABSTRACT

An adjustable light therapy care electric toothbrush is provided, including a toothbrush head and a toothbrush handle. A second circuit board assembly is built in the toothbrush head, an NFC chip and a memory are encapsulated on the second circuit board assembly, a signal receiving antenna is arranged in the toothbrush head, a first circuit board assembly is built in the toothbrush handle, a card reading chip is encapsulated on the first circuit board assembly, the card reading chip is in wireless signal communication with the NFC chip, and functional loads are arranged in the toothbrush head and electrically connected to the second circuit board assembly. According to the adjustable light therapy care electric toothbrush, encapsulating the NFC chip and the memory in the toothbrush head, encapsulating the card reading chip in the toothbrush handle and achieving wireless signal control through the card reading chip and the NFC chip.

9 Claims, 2 Drawing Sheets

ADJUSTABLE LIGHT THERAPY CARE ELECTRIC TOOTHBRUSH

CROSS-REFERENCE TO RELATED APPLICATIONS

The application claims priority to Chinese patent application No. 2025213765217, filed on Jul. 2, 2025, the entire contents of which are incorporated herein by reference.

TECHNICAL FIELD

The present disclosure relates to the technical field of toothbrushes, and in particular, to an adjustable light therapy care electric toothbrush.

BACKGROUND

As a cleaning product and a handle-type brush, the toothbrush is used to repeatedly brush various parts of the teeth after adding toothpaste to the brush, to maintain oral hygiene.

The toothbrush can clean stains on the surface of teeth very well, but it is not capable of deeper oral cleaning and care. For example, penetrative yellow teeth cannot be significantly removed by toothpaste or essence. For another example, for periodontitis, gingivitis, etc., it is often necessary to take medicine or spray anti-inflammatory liquid to achieve a certain therapeutic effect. Although these traditional methods can solve the user's troubles to a certain extent, the essence, medicine, anti-inflammatory liquid and the like used in the mouth will more or less enter the human internal organs through the mouth, thereby causing harm to human health. This is not advocated unless it is necessary.

Therefore, in addition to the basic cleaning function, traditional toothbrushes cannot meet more oral care needs of users.

In order to improve the cleaning and care effect of the toothbrush, light therapy lamp beads, ultrasonic cleaning modules and the like will be placed in toothbrush heads, but these functional loads need to be driven by power when working, which is not difficult to achieve for an integrated toothbrush. The functional loads of the integrated toothbrush can be powered through a built-in battery and internal wiring. However, this implementation is very difficult for the structure of the electric toothbrush. On the one hand, the space of the toothbrush body is limited, so the toothbrush cannot load electrical components with a total volume that is too large, and on the other hand, the technical problems of wireless power supply and wireless signal control also need to be solved. At present, in electric toothbrushes, wireless power supply has been achieved by setting a wireless power receiving coil and a power transmitting coil between two relatively independent components (the toothbrush head and the toothbrush handle), such that the electric energy of the battery built in the toothbrush handle is supplied to the functional loads for use. However, the technical problem of wireless signal control has not been solved so far. Commonly used wireless signal controls include Bluetooth technology and infrared technology. In addition to the high cost and large volume occupation, the Bluetooth technology also has a defect of high power consumption. The storage capacity of the built-in battery of the electric toothbrush itself cannot support the use of Bluetooth for a long time. The infrared technology requires that a receiving end must form an illuminating surface or a refracted illuminating surface with a transmitting path to achieve signal reception, which is basically impossible to achieve with the structural characteristics of the electric toothbrush. Therefore, for the current electric toothbrush loaded with functional loads, the functional loads often achieve a single working mode, and the single working mode is often directly triggered after the internal circuit of the toothbrush head is connected. Users cannot switch and adjust the functional mode according to actual usage needs. Therefore, the current electric toothbrush loaded with the functional loads is very useless in actual use.

SUMMARY

An objective of the present disclosure is to provide an adjustable light therapy care electric toothbrush. Encapsulating an NFC (Near Field Communication) chip and a memory in a toothbrush head, encapsulating a card reading chip in a toothbrush handle and achieving wireless signal control through the card reading chip and the NFC chip can not only achieve the application advantages of low power consumption, low cost and small volume, but also achieve switching and regulation of multiple modes of the functional loads built in the toothbrush head, thereby improving the practicality and care efficacy of the product and solving the problems proposed in the above-mentioned background.

To achieve the above-mentioned objective, the present disclosure provides the following technical solutions: an adjustable light therapy care electric toothbrush, including a toothbrush head and a toothbrush handle, the toothbrush head being detachably connected to the toothbrush handle, where a second circuit board assembly is built in the toothbrush head, an NFC chip and a memory are encapsulated on the second circuit board assembly, a signal receiving antenna is arranged in the toothbrush head, the NFC chip is in signal communication with the signal receiving antenna, a first circuit board assembly is built in the toothbrush handle, a card reading chip is encapsulated on the first circuit board assembly, the card reading chip is in wireless signal communication with the NFC chip, functional loads are arranged in the toothbrush head and electrically connected to the second circuit board assembly, and the second circuit board assembly electrically communicates with the first circuit board assembly through an electrical connection mechanism.

Preferably, a brush head body is arranged at one end of the toothbrush head, and a connecting end piece is arranged at the other end of the toothbrush head. The toothbrush head is detachably connected to an output shaft of a driving motor on the toothbrush handle through the connecting end piece. The brush head body includes a brush head accommodating cavity and a bristle base covered at a cavity opening of the brush head accommodating cavity. Bristles are arranged on the side of the bristle base away from the brush head accommodating cavity. The second circuit board assembly is arranged in the brush head accommodating cavity. The functional loads are light therapy lamp beads that are encapsulated on the second circuit board assembly. Light emitting directions of the light therapy lamp beads are arranged toward one side of the bristle base, and the bristle base is a light-transmitting member and/or the bristles are light-guiding fibers.

Preferably, the bristle base is water-sealed at the cavity opening of the brush head accommodating cavity, the end of the bristles away from the brush head accommodating cavity extends out of the bristle base, and the end of the bristles facing the brush head accommodating cavity penetrates through the bristle base and communicates with the brush head accommodating cavity.

Preferably, a reflective layer is covered on an inner surface of the brush head accommodating cavity.

Preferably, the light therapy lamp beads include blue-light lamp beads and red-light lamp beads, the blue-light lamp beads have a ray wavelength of 400-460 nm, and the red-light lamp beads have a ray wavelength of 630-660 nm.

Preferably, the electrical connection mechanism includes a power receiving coil arranged in the toothbrush head and a power transmitting coil arranged on the toothbrush handle, the power receiving coil is wirelessly and electrically connected to the power transmitting coil, and the signal receiving antenna is the power receiving coil.

Preferably, the toothbrush head includes a toothbrush head shell, one end of which forms the brush head accommodating cavity and the other end of which forms a conical cavity, the connecting end piece is embedded in the conical cavity, and the power receiving coil is arranged on the side of the connecting end piece facing the conical cavity. The toothbrush handle includes a handle shell that is a sleeve shell with both ends opened, an upper-end plug is arranged at an upper-end opening of the handle shell, the driving motor is mounted inside the handle shell, the output shaft of the driving motor passes through the upper-end plug and extends outward from the upper-end opening of the handle shell, the power transmitting coil is arranged on the upper-end plug, and the power receiving coil is wirelessly and electrically connected to the power transmitting coil.

Preferably, an electrical appliance bracket is arranged in the handle shell, the first circuit board assembly and a battery are arranged in the handle shell, the driving motor, the battery and the circuit board assembly are all fixedly mounted on the electrical appliance bracket, a waterproof cover is encapsulated at the upper-end opening of the handle shell, the waterproof cover is sleeved on a circumference of the output shaft of the driving motor and clamped between the upper-end plug and the handle shell, a bottom-end plug is encapsulated at a lower-end opening of the handle shell, a power input interface is arranged on the bottom-end plug, and the power input interface is electrically connected to the circuit board assembly.

Preferably, the first circuit board assembly is electrically connected to control buttons and indicator lights, and the control buttons and indicator lights are both arranged in through holes preset in the handle shell.

Preferably, the electrical appliance bracket includes a motor bracket and a battery bracket, and the motor bracket and the battery bracket are plug-connected at opposite ends.

Compared with the existing technology, the beneficial effects of the present disclosure are:

According to the adjustable light therapy care electric toothbrush, encapsulating the NFC chip and the memory in the toothbrush head, encapsulating the card reading chip in the toothbrush handle and achieving wireless signal control through the card reading chip and the NFC chip can not only achieve the application advantages of low power consumption, low cost and small volume, but also achieve switching and regulation of multiple modes of the functional loads built in the toothbrush head, thereby improving the practicality and care efficacy of the product.

Figure 1:
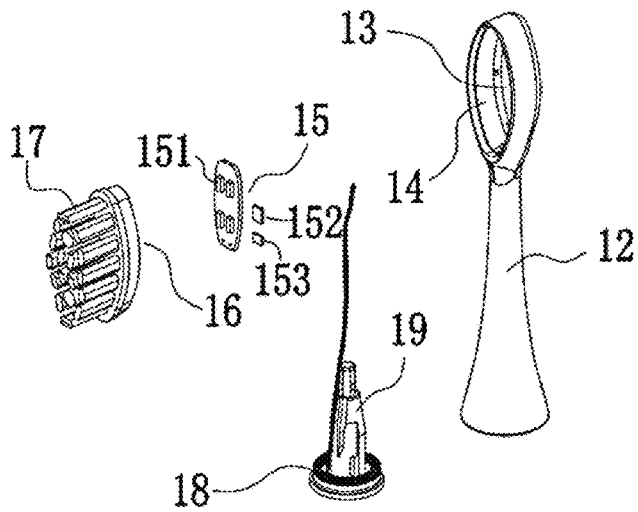
FIG. 1 is an exploded structural view according to the present disclosure.
Figure 1:
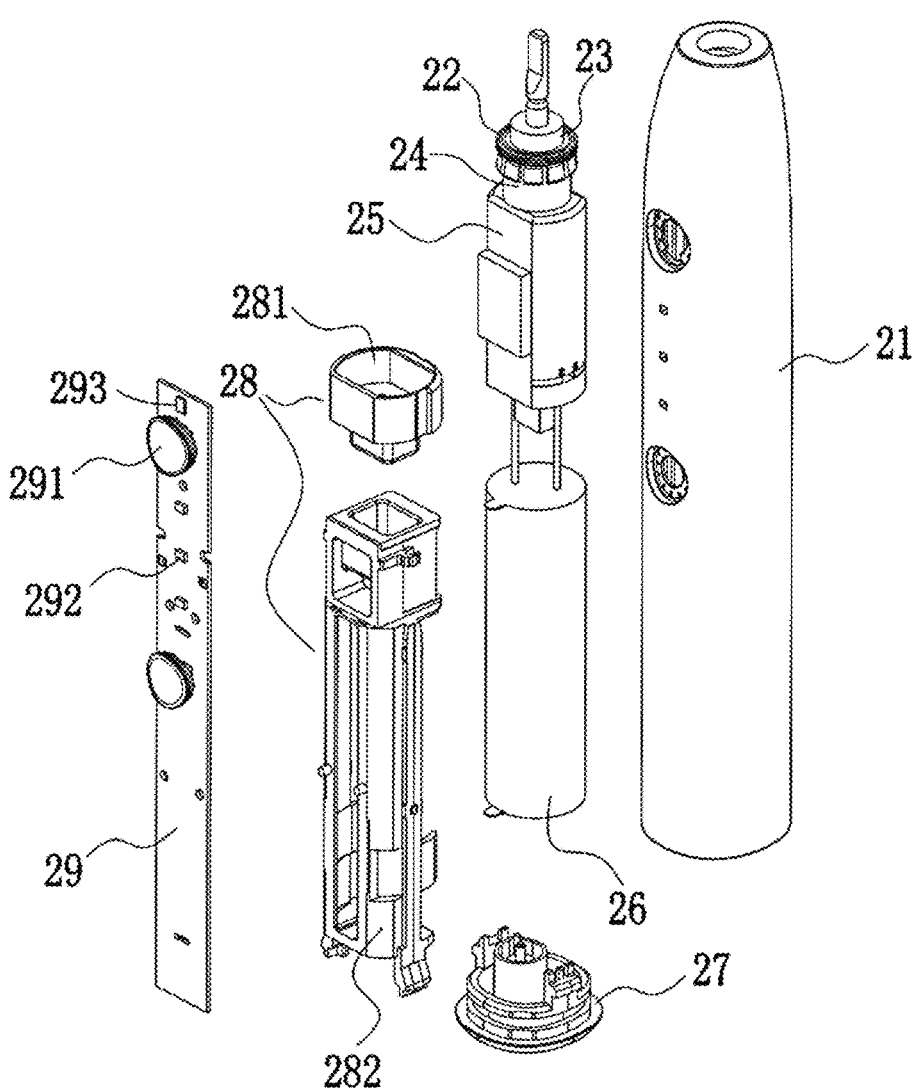

In the figure: toothbrush head 1; brush head body 11; toothbrush head shell 12; brush head accommodating cavity 13; reflective layer 14; second circuit board assembly 15; light therapy lamp bead 151; NFC chip 152; memory 153; bristle base 16; bristles 17; power receiving coil 18; connecting end piece 19; toothbrush handle 2; handle shell 21; power transmitting coil 22; waterproof cover 23; upper-end plug 24; driving motor 25; battery 26; bottom-end plug 27; electrical appliance bracket 28; motor bracket 281; battery bracket 282; first circuit board assembly 29; control button 291; indicator light 292; card reading chip 293.

DETAILED DESCRIPTION OF THE EMBODIMENTS

The technical solutions in the embodiments of the present disclosure are clearly and completely elaborated below in combination with the drawings in the embodiments of the present disclosure. It is apparent that the described embodiments are only a part of the embodiments of the present disclosure but not all. Based on the embodiments of the present disclosure, all the other embodiments obtained by those of ordinary skill in the art on the premise of not contributing creative effort should belong to the protection scope of the present disclosure.

Figure 2:
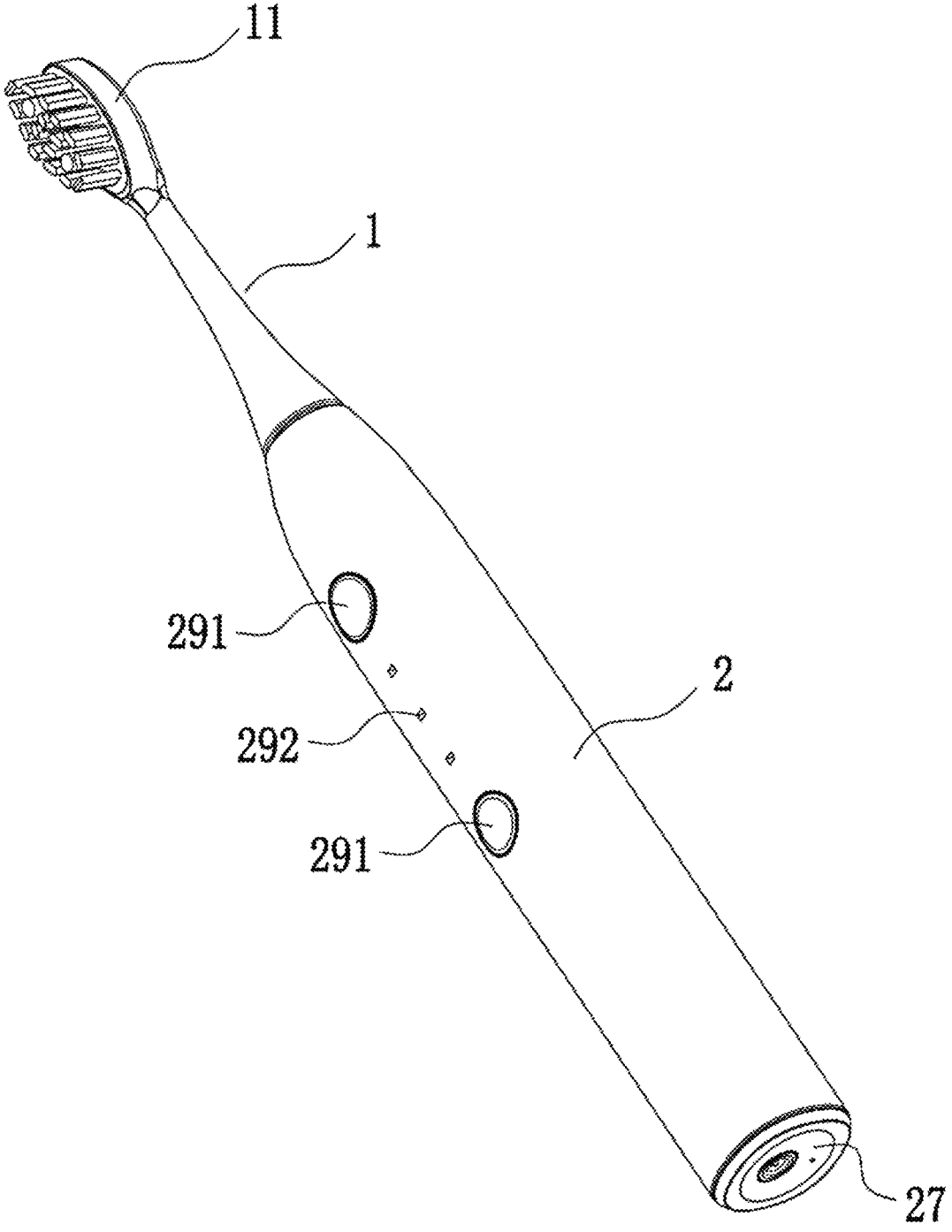
FIG. 2 is a schematic structural diagram according to the present disclosure.

Referring to FIGS. 1 to 2, an adjustable light therapy care electric toothbrush includes a toothbrush head 1 and a toothbrush handle 2. The he toothbrush head 1 is detachably connected to the toothbrush handle 2, a brush head body 11 is arranged at one end of the toothbrush head 1, and a connecting end piece 19 is arranged at the other end of the toothbrush head 1. The toothbrush head 1 is detachably connected to an output shaft of a driving motor 25 on the toothbrush handle 2 through the connecting end piece 19. The brush head body 11 includes a brush head accommodating cavity 13 and a bristle base 16 covered at a cavity opening of the brush head accommodating cavity 13, the bristle base 16 is encapsulated at the cavity opening of the brush head accommodating cavity 13 by an ultrasonic process, the bristle base 16 is in water-sealed connection with the brush head accommodating cavity 13, bristles 17 are arranged on the side of the bristle base 16 away from the brush head accommodating cavity 13, the end of the bristles 17 away from the brush head accommodating cavity 13 extends out of the bristle base 16, and the end of the bristles 17 facing the brush head accommodating cavity 13 penetrates through the bristle base 16 and communicates with the brush head accommodating cavity 13. Functional loads are arranged in the toothbrush head 1. In this embodiment, the functional loads are light therapy lamp beads 151. A second circuit board assembly 15 is arranged in the brush head accommodating cavity 13, the light therapy lamp beads 151 are encapsulated on the second circuit board assembly 15. The light therapy lamp beads 151 include blue-light lamp beads and red-light lamp beads, the blue-light lamp beads have a ray wavelength of 400-460 nm, and the red-light lamp beads have a ray wavelength of 630-660 nm. The blue light in this waveband can effectively whiten teeth, and the red light in this waveband can effectively perform oral anti-inflammatory care. Light emitting directions of the light therapy lamp beads 151 are arranged toward one side of the bristle base 16, and a reflective layer 14 is covered on an inner surface of the brush head accommodating cavity 13. The reflective layer 14 can irradiate the reflected ray of the diffuse reflection part of the light therapy lamp beads 151 to the direction where the bristle base 16 is located to enhance the intensity of the light source. The bristle base 16 is a light-transmitting element. The refractive index of the bristle base 16 can be adjusted according to the actual lighting range requirements during product design, to increase or decrease the irradiation area of the light therapy ray. The bristles 17 are light-guiding fibers. The light-guiding fibers can guide the ray efficiently and accurately to act on the teeth, which is beneficial to improving the light therapy care effect and reducing the propagation loss of the ray. An NFC chip 152 and a memory 153 are encapsulated on the second circuit board assembly 15, a signal receiving antenna is arranged in the toothbrush head 1, the NFC chip 152 is in signal communication with the signal receiving antenna, a first circuit board assembly 29 is built in the toothbrush handle 2, a card reading chip 293 is encapsulated on the first circuit board assembly 29, the card reading chip 293 is in wireless signal communication with the NFC chip 152, the memory 153 is configured to store a control signal and a software control procedure, the card reading chip 293 sends the control signal to the NFC chip 152 after reading the user's operating instruction, the signal receiving antenna delivers the received control signal to the NFC chip, the NFC chip 152 triggers the functional loads according to the control signal to start the corresponding working mode, and the toothbrush head 1 electrically communicates with the toothbrush handle 2 through an electrical connection mechanism. The electrical connection mechanism includes a power receiving coil 18 arranged in the toothbrush head 1 and a power transmitting coil 22 arranged on the toothbrush handle 2, and the power receiving coil 18 is wirelessly and electrically connected to the power transmitting coil 22. In this embodiment, the power receiving coil 18 can also be used as the signal receiving antenna for the NFC chip 152.

The toothbrush head 1 includes a toothbrush head shell 12, one end of which forms the brush head accommodating cavity 13 and the other end of which forms a conical cavity, the connecting end piece 19 is embedded in the conical cavity, and the power receiving coil 18 is arranged on the side of the connecting end piece 19 facing the conical cavity. The toothbrush handle 2 includes a handle shell 21 that is a sleeve shell with both ends opened, an upper-end plug 24 is arranged at an upper-end opening of the handle shell 21, the driving motor 25 is mounted inside the handle shell 21, the output shaft of the driving motor 25 passes through the upper-end plug 24 and extends outward from the upper-end opening of the handle shell, the power transmitting coil 22 is arranged on the upper-end plug 24, and the power receiving coil 18 is wirelessly and electrically connected to the power transmitting coil 22.

An electrical appliance bracket 28 is arranged in the handle shell 21, the electrical appliance bracket 28 includes a motor bracket 281 and a battery bracket 282, and the motor bracket 281 and the battery bracket 282 are plug-connected at opposite ends. The first circuit board assembly 29 and a battery 26 are arranged in the handle shell 21, the driving motor 25, the battery 26 and the circuit board assembly 29 are all fixedly mounted on the electrical appliance bracket 28, a waterproof cover 23 is encapsulated at the upper-end opening of the handle shell 21, the waterproof cover 23 is sleeved on a circumference of the output shaft of the driving motor and clamped between the upper-end plug 24 and the handle shell 21, a bottom-end plug 27 is encapsulated at a lower-end opening of the handle shell 21, a power input interface is arranged on the bottom-end plug 27, and the power input interface is electrically connected to the circuit board assembly 29. The first circuit board assembly 29 is electrically connected to control buttons 291 and indicator lights 292, and the control buttons 291 and indicator lights 292 are both arranged in through holes preset in the handle shell 21. The control buttons 291 are configured to adjust the working mode of the driving motor 25 and the working mode of the light therapy lamp beads 151, and the indicator lights 292 are configured to display the real-time working mode of the electric toothbrush.

In summary: according to the adjustable light therapy care electric toothbrush, encapsulating the NFC chip 152 and the memory 153 in the toothbrush head 1, encapsulating the card reading chip 293 in the toothbrush handle 2 and achieving wireless signal control through the card reading chip 293 and the NFC chip 152 can not only achieve the application advantages of low power consumption, low cost and small volume, but also achieve switching and regulation of multiple modes of the functional loads built in the toothbrush head 1, thereby improving the practicality and care efficacy of the product.

It is noted that, in this text, relational terms "first", "second" and the like are merely used for separating one entity or operation from another entity or operation, rather than not necessarily requiring or implying any actual relation or sequence between the entity and the operation. In addition, terms "include" and "comprise" or any other variant are intended to cover nonexclusive inclusions herein, so that a process, method, goods or device including a series of elements not only includes those elements but also includes other elements which are not clearly listed or further includes elements intrinsic to the process, the method, the goods or the device.

Although the embodiments of the present disclosure have been presented and described, those of ordinary skill in the art may understand that various changes, modifications, replacements and deformations can be made to these embodiments without deviating from the principle of spirit of the present disclosure, and the scope of the present disclosure is defined by the appended claims and their equivalents.

What is claimed is:

1. An adjustable light therapy care electric toothbrush, comprising a toothbrush head (1) and a toothbrush handle (2), the toothbrush head (1) being detachably connected to the toothbrush handle (2), wherein a second circuit board assembly (15) is built in the toothbrush head (1), an NFC chip (152) and a memory (153) are encapsulated on the second circuit board assembly (15), a signal receiving antenna is arranged in the toothbrush head (1), the NFC chip (152) is in signal communication with the signal receiving antenna, a first circuit board assembly (29) is built in the toothbrush handle (2), a card reading chip (293) is encapsulated on the first circuit board assembly (29), the card reading chip (293) is in wireless signal communication with the NFC chip (152), functional loads are arranged in the toothbrush head (1) and electrically connected to the second circuit board assembly (15), and the second circuit board assembly (15) electrically communicates with the first circuit board assembly (29) through an electrical connection mechanism;

wherein the electrical connection mechanism comprises a power receiving coil (18) arranged in the toothbrush head (1) and a power transmitting coil (22) arranged on the toothbrush handle (2), the power receiving coil (18) is wirelessly and electrically connected to the power transmitting coil (22), and the signal receiving antenna is the power receiving coil (18).

2. The adjustable light therapy care electric toothbrush according to claim 1, wherein a brush head body (11) is arranged at one end of the toothbrush head (1), and a connecting end piece (19) is arranged at the other end of the toothbrush head (1); the toothbrush head (1) is detachably connected to an output shaft of a driving motor (25) on the toothbrush handle (2) through the connecting end piece (19), the brush head body (11) comprises a brush head accommodating cavity (13) and a bristle base (16) covered at a cavity opening of the brush head accommodating cavity (13), bristles (17) are arranged on the side of the bristle base (16) away from the brush head accommodating cavity (13), the second circuit board assembly (15) is arranged in the brush head accommodating cavity (13), the functional loads are light therapy lamp beads (151) that are encapsulated on the second circuit board assembly (15), light emitting directions of the light therapy lamp beads (151) are arranged toward one side of the bristle base (16), and the bristle base (16) is a light-transmitting member and/or the bristles (17) are light-guiding fibers.

3. The adjustable light therapy care electric toothbrush according to claim 2, wherein the bristle base (16) is water-sealed at the cavity opening of the brush head accommodating cavity (13), the end of the bristles (17) away from the brush head accommodating cavity (13) extends out of the bristle base (16), and the end of the bristles (17) facing the brush head accommodating cavity (13) penetrates through the bristle base (16) and communicates with the brush head accommodating cavity (13).

4. The adjustable light therapy care electric toothbrush according to claim 2, wherein a reflective layer (14) is covered on an inner surface of the brush head accommodating cavity (13).

5. The adjustable light therapy care electric toothbrush according to claim 2, wherein the light therapy lamp beads (151) comprise blue-light lamp beads and red-light lamp beads, the blue-light lamp beads have a ray wavelength of 400-460 nm, and the red-light lamp beads have a ray wavelength of 630-660 nm.

6. The adjustable light therapy care electric toothbrush according to claim 2, wherein the toothbrush head (1) comprises a toothbrush head shell (12), one end of which forms the brush head accommodating cavity (13) and the other end of which forms a conical cavity, the connecting end piece (19) is embedded in the conical cavity, and the power receiving coil (18) is arranged on the side of the connecting end piece (19) facing the conical cavity; the toothbrush handle (2) comprises a handle shell (21) that is a sleeve shell with both ends opened, an upper-end plug (24) is arranged at an upper-end opening of the handle shell (21), the driving motor (25) is mounted inside the handle shell (21), the output shaft of the driving motor (25) passes through the upper-end plug (24) and extends outward from the upper-end opening of the handle shell, the power transmitting coil (22) is arranged on the upper-end plug (24), and the power receiving coil (18) is wirelessly and electrically connected to the power transmitting coil (22).

7. The adjustable light therapy care electric toothbrush according to claim 6, wherein an electrical appliance bracket (28) is arranged in the handle shell (21), the first circuit board assembly (29) and a battery (26) are arranged in the handle shell (21), the driving motor (25), the battery (26) and the circuit board assembly (29) are all fixedly mounted on the electrical appliance bracket (28), a waterproof cover (23) is encapsulated at the upper-end opening of the handle shell (21), the waterproof cover (23) is sleeved on a circumference of the output shaft of the driving motor and clamped between the upper-end plug (24) and the handle shell (21), a bottom-end plug (27) is encapsulated at a lower-end opening of the handle shell (21), a power input interface is arranged on the bottom-end plug (27), and the power input interface is electrically connected to the circuit board assembly (29).

8. The adjustable light therapy care electric toothbrush according to claim 7, wherein the first circuit board assembly (29) is electrically connected to control buttons (291) and indicator lights (292), and the control buttons (291) and indicator lights (292) are both arranged in through holes preset in the handle shell (21).

9. The adjustable light therapy care electric toothbrush according to claim 7, wherein the electrical appliance bracket (28) comprises a motor bracket (281) and a battery bracket (282), and the motor bracket (281) and the battery bracket (282) are plug-connected at opposite ends.

* * * * *